(12) United States Patent
Matsushita

(10) Patent No.: US 11,406,245 B2
(45) Date of Patent: Aug. 9, 2022

(54) OVERTUBE

(71) Applicant: FUJIFILM Corporation, Tokyo (JP)

(72) Inventor: Motohiko Matsushita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 239 days.

(21) Appl. No.: 16/840,455

(22) Filed: Apr. 6, 2020

(65) Prior Publication Data

US 2020/0245847 A1 Aug. 6, 2020

Related U.S. Application Data

(63) Continuation of application No. PCT/JP2018/037137, filed on Oct. 4, 2018.

(30) Foreign Application Priority Data

Oct. 11, 2017 (JP) .............................. JP2017-197541

(51) Int. Cl.
*A61B 1/00* (2006.01)
*A61B 1/12* (2006.01)

(52) U.S. Cl.
CPC ...... *A61B 1/00082* (2013.01); *A61B 1/00135* (2013.01); *A61B 1/12* (2013.01)

(58) Field of Classification Search
None
See application file for complete search history.

(56) References Cited

U.S. PATENT DOCUMENTS

| 5,556,411 A | 9/1996 | Taoda et al. |
| 7,143,925 B2 | 12/2006 | Shelton, IV et al. |
| 8,088,063 B2 | 1/2012 | Fujikura et al. |
| 8,092,372 B2 | 1/2012 | Machida |

(Continued)

FOREIGN PATENT DOCUMENTS

| CN | 1101538 | 4/1995 |
| CN | 1628600 | 6/2005 |

(Continued)

OTHER PUBLICATIONS

"International Search Report (Form PCT/ISA/210)" of PCT/JP2018/037137, dated Dec. 25, 2018, with English translation thereof, pp. 1-3.

(Continued)

*Primary Examiner* — Timothy J Neal
(74) *Attorney, Agent, or Firm* — JCIPRNET

(57) ABSTRACT

There is provided an overtube that can suppress contact of an opening edge portion of a ventilation hole of the overtube with a lumen inner wall surface. The overtube includes an overtube body that has a distal end and a proximal end and allows an insertion part of an endoscope, which is to be inserted into a lumen, to be inserted therein, a balloon that is mounted on an outer circumferential surface of the overtube body, a protruding part that is formed on the outer circumferential surface, and an ventilation hole that is formed in the outer circumferential surface and allows the outer circumferential surface and an inner circumferential surface of the overtube body to communicate with each other. On the outer circumferential surface, one of the protruding part or the ventilation hole is formed in a peripheral portion of the other.

9 Claims, 14 Drawing Sheets

(56) References Cited

U.S. PATENT DOCUMENTS

| | | |
|---|---|---|
| 8,251,900 B2 | 8/2012 | Ortiz et al. |
| 8,721,526 B2 | 5/2014 | Fujikura |
| 9,125,685 B2 | 9/2015 | Pauli et al. |
| 9,433,759 B2 | 9/2016 | Fujikura et al. |
| 10,398,523 B2 | 9/2019 | Roesler et al. |
| 10,448,803 B2 | 10/2019 | Iwasaka |
| 11,173,007 B2 | 11/2021 | Roesler et al. |
| 2006/0252992 A1 | 11/2006 | Mitsumori |
| 2007/0299308 A1 | 12/2007 | Fujikura et al. |
| 2008/0281155 A1 | 11/2008 | Fujikura |
| 2008/0294004 A1 | 11/2008 | Fujikura |
| 2009/0023996 A1 | 1/2009 | Fujikura |
| 2009/0275919 A1 | 11/2009 | Todd et al. |
| 2012/0220829 A1* | 8/2012 | Fujikura ................ A61B 1/015 600/115 |
| 2015/0342579 A1 | 12/2015 | Heske et al. |

FOREIGN PATENT DOCUMENTS

| | | |
|---|---|---|
| CN | 1636499 | 7/2005 |
| CN | 1745719 | 3/2006 |
| CN | 101301190 | 11/2008 |
| CN | 101347321 | 1/2009 |
| CN | 101785656 | 7/2010 |
| CN | 101822554 | 9/2010 |
| CN | 102015003 | 4/2011 |
| CN | 103505173 | 1/2014 |
| CN | 105188506 | 12/2015 |
| CN | 107049510 | 8/2017 |
| EP | 2364637 | 9/2011 |
| JP | H0724056 | 1/1995 |
| JP | H10155733 | 6/1998 |
| JP | 2004016544 | 1/2004 |
| JP | 2004261431 | 9/2004 |
| JP | 2005211435 | 8/2005 |
| JP | 3804068 | 8/2006 |
| JP | 2009022443 | 2/2009 |
| JP | 2011188898 | 9/2011 |
| JP | 2012045254 | 3/2012 |
| JP | 2014073279 | 4/2014 |
| WO | 2010002733 | 1/2010 |

OTHER PUBLICATIONS

"Written Opinion of the International Searching Authority (Form PCT/ISA/237)" of PCT/JP2018/037137, dated Dec. 25, 2018, with English translation thereof, pp. 1-11.

"Office Action of China Counterpart Application" with English translation thereof, dated Nov. 15, 2021, p. 1-p. 20.

* cited by examiner

OVERTUBE

CROSS-REFERENCE TO RELATED APPLICATIONS

The present application is a Continuation of PCT International Application No. PCT/JP2018/037137 filed on Oct. 4, 2018 claiming priority under 35 U.S.C. § 119(a) to Japanese Patent Application No. 2017-197541 filed on Oct. 11, 2017. Each of the above applications is hereby expressly incorporated by reference, in its entirety, into the present application.

BACKGROUND OF THE INVENTION

1. Field of the Invention

The present invention relates to an overtube that is inserted into a body lumen along with an insertion part of an endoscope.

2. Description of the Related Art

In the related art, a technique of inserting an insertion part of an endoscope into a digestive tract (lumen) such as the large intestine and the small intestine and executing observation, diagnosis, treatment of an inner wall surface of the digestive tract is performed in the medical field. The digestive tract such as the large intestine and the small intestine is bent in a complicated manner. Thus, it is difficult to transmit a force to a distal end of the insertion part simply by pushing the insertion part of the endoscope, and it is difficult to insert the endoscope into a deep portion.

Thus, a so-called double-balloon endoscope device, in which an inflatable and deflateable balloon is provided at each of an insertion part of an endoscope and a distal end portion of an overtube covered with the insertion part, is known. In the endoscope device, a balloon control device can be individually controlled the inflation and deflation of each balloon by supplying and sucking air into and from each balloon. Accordingly, the insertion part can be inserted into a deep portion of the digestive tract bent in a complicated manner by alternately inserting the insertion part and the overtube while temporarily fixing each balloon to the digestive tract individually at a predetermined timing.

In the technique using such an endoscope device, as an operator operates the overtube to be pulled to a hand side in a state where a balloon of the overtube is inflated and the balloon is closely attached to an inner wall surface of the digestive tract, the digestive tract is dragged to the hand side. In this case, a gas accumulated on a back side (removal direction) of the balloon [an existing gas in the intestine and a gas (air or a carbon dioxide gas) supplied from the endoscope] is compressed to increase an internal pressure of the intestinal tract, and the overtube cannot be moved to the hand side due to the resistance of operation of pulling the overtube. Thus, there is a possibility of obstructing the technique.

In each of overtubes disclosed in JP1998-155733A (JP-H10-155733A), JP3804068B, JP2009-022443A, and JP2011-188898A, a ventilation hole is provided in an outer circumferential surface of the overtube behind a balloon. The ventilation hole communicates with the inside of a lumen and the outside of the lumen (outside the body). In the overtube, even when a gas is trapped in a region created by, for example, the anus or the pylorus, the outer circumferential surface of the overtube, and the balloon, the gas escapes from the ventilation hole to the outside of the body in a case where the overtube is pulled to the hand side. Thus, the digestive tract can be prevented from being pressed.

SUMMARY OF THE INVENTION

However, in a case where the overtube of each of JP1998-155733A (JP-H10-155733A), JP3804068B, JP2009-022443A, and JP2011-188898A is used, there is a possibility that an opening edge portion of the ventilation hole of the overtube slides on a lumen inner wall surface when inserting the overtube into the lumen, withdrawing the overtube from the lumen, or moving the overtube forward and backward in the lumen.

The present invention is devised in view of such circumstances, and an object thereof is to provide an overtube that can suppress contact of an opening edge portion of a ventilation hole of the overtube with a lumen inner wall surface.

According to an aspect of the present invention, to achieve the object, there is provided an overtube comprising an overtube body that has a distal end and a proximal end and allows an insertion part of an endoscope, which is to be inserted into a lumen, to be inserted therein, a balloon that is mounted on an outer circumferential surface of the overtube body, a protruding part that is formed on the outer circumferential surface, and a ventilation hole that is formed in the outer circumferential surface and allows the outer circumferential surface and an inner circumferential surface of the overtube body to communicate with each other. On the outer circumferential surface, one of the protruding part or the ventilation hole is formed in a peripheral portion of the other. The peripheral portion is a region where a gap is secured between the inner wall surface of the lumen and the ventilation hole in the outer circumferential surface of the overtube body as the protruding part comes into contact with the inner wall surface of the lumen, that is, a contact restricting region where contact with the inner wall surface of the lumen is restricted by the protruding part.

In the overtube, in a case where one of an opening edge portion of the ventilation hole or the inner wall surface of the lumen relatively approaches the other, the protruding part functions as a spacer restricting contact between the opening edge portion of the ventilation hole and the inner wall surface of the lumen. Thus, contact of the opening edge portion of the ventilation hole with the inner wall surface of the lumen is prevented.

In the overtube according to another aspect of the present invention, the ventilation hole is formed closer to a proximal end side of the overtube body than the balloon is.

In the overtube according to another aspect of the present invention, an annular fixing part that fixes an end part of the balloon, which is positioned closer to a proximal end side of the overtube body than a bulging part of the balloon is, to the outer circumferential surface is provided on the outer circumferential surface. An outer diameter of the annular fixing part is formed to be larger than an outer diameter of the outer circumferential surface. The protruding part is the annular fixing part. Accordingly, since the protruding part can perform both of the fixing of the balloon and the prevention of contact of the opening edge portion of the ventilation hole with the inner wall surface of the lumen, an increase in the number of components of the overtube is suppressed.

In the overtube according to another aspect of the present invention, an air supply and discharge pipe line that allows air to be supplied and discharged into and from an inside of the balloon is formed between the outer circumferential surface and the inner circumferential surface of the overtube body along a central axis of the overtube body. On the outer circumferential surface, a first region corresponding to a portion where the air supply and discharge pipe line is formed is upheaved higher than a second region corresponding to the other portion. The protruding part is the first region. Accordingly, an increase in the number of components of the overtube is suppressed since the existing air supply and discharge pipe line is used as the protruding part.

In the overtube according to another aspect of the present invention, the protruding part has an annular shape that surrounds an opening of the ventilation hole in the outer circumferential surface. Accordingly, contact of the opening edge portion of the ventilation hole with the inner wall surface of the lumen can be prevented, and a degree of freedom of a position of the ventilation hole can be increased.

In the overtube according to another aspect of the present invention, two annular protruding parts having a shape following a circumferential direction of the outer circumferential surface are formed on the outer circumferential surface of the overtube body at an interval along a central axis of the overtube body. The ventilation hole is opened between two protruding parts on the outer circumferential surface. Accordingly, contact of the opening edge portion of the ventilation hole with the inner wall surface of the lumen is prevented.

In the overtube according to another aspect of the present invention, a surface of the protruding part, which faces an inner wall surface of the lumen, is formed by a curved surface. Accordingly, the protruding part can be smoothly brought into contact with the inner wall surface of the lumen.

In the overtube according to another aspect of the present invention, the ventilation hole has a circular shape having a diameter of 1 mm to 5 mm. Accordingly, the prevention of clogging of the ventilation hole attributable to a residue, the prevention of a kink of the overtube body, and the suppression of infiltration of the residue from the ventilation hole into the overtube body are achieved.

In the overtube according to another aspect of the present invention, there is a gripping part gripped by an operator on a proximal end side of the overtube body. A gripping part outer circumferential surface of the gripping part is included in the outer circumferential surface, and a gripping part inner circumferential surface of the gripping part is included in the inner circumferential surface. The overtube further comprises a gripping part ventilation hole that allows the gripping part inner circumferential surface and the gripping part outer circumferential surface of the gripping part to communicate with each other. Accordingly, the operator can perform operation of the endoscope without paying attention to a bodily fluid discharged from the proximal end of the overtube.

In the overtube according to still another aspect of the present invention, a porous film that selectively allows air to pass therethrough is provided in the ventilation hole. Accordingly, a residue is prevented from infiltrating into the overtube body from the ventilation hole.

In the present invention, contact of the opening edge portion of the ventilation hole of the overtube with the lumen inner wall surface can be suppressed.

DESCRIPTION OF THE PREFERRED EMBODIMENTS

Hereinafter, an overtube according to preferable embodiments of the present invention will be described in detail with reference to the accompanying drawings.

First Embodiment

Figure 1:
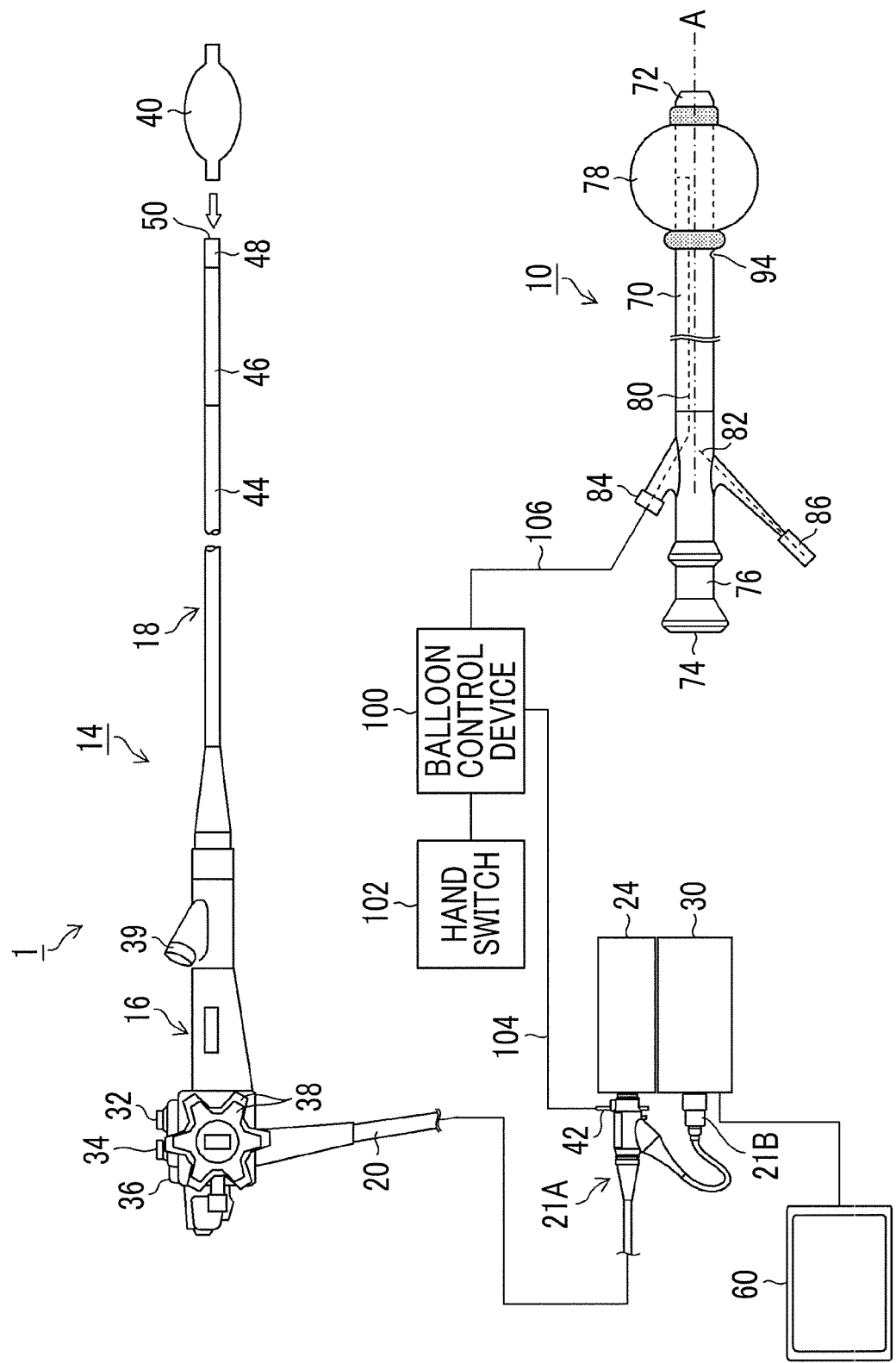
FIG. 1 is a system configuration view of an endoscope device having an overtube according to a first embodiment of the present invention.

FIG. 1 is a system configuration view of an endoscope device 1 having an overtube 10 according to a first embodiment of the present invention.

The endoscope device 1 illustrated in FIG. 1 comprises, for example, a flexible endoscope 14 for the upper digestive tract, for the lower digestive tract, or for the small intestine, the overtube 10, and a balloon control device 100.

The endoscope 14 comprises a hand operation part 16 and an insertion part 18 which is installed consecutively to the hand operation part 16. A universal cable 20 is connected to the hand operation part 16. Although not illustrated, the universal cable 20 includes a signal cable, a light guide, and an air supply tube. At a distal end of the universal cable 20, a connector 21A connected to a light source device 24, a connector 21B that is branched from the connector 21A and is connected to a processor 30 are provided. A monitor 60 is connected to the processor 30.

The connector 21A is provided with a balloon air supply port 42 for supplying air to a balloon 40 to be described later or for sucking air from the balloon 40. The "air" herein is a gas for inflating the balloon 40 (also including a balloon 78 to be described later), and a type (component) thereof is not particularly limited.

In addition, in the hand operation part 16, an air supply and water supply button 32, a suction button 34, and a shutter button 36 are arranged to be parallel to each other, and a pair of angle knobs 38 and a forceps insertion part 39 are provided.

The insertion part 18 is inserted into, for example, a lumen 160 (refer to FIG. 6) of the small intestine and the large intestine. The insertion part 18 is configured by a flexible portion 44, a curved portion 46, and a distal end portion 48 from a proximal end side toward a distal end side. The curved portion 46 is remotely curved by moving the pair of angle knobs 38 provided in the hand operation part 16 rotationally. Accordingly, a distal end surface 50 of the distal end portion 48 can be directed in a desired direction.

Figure 2:
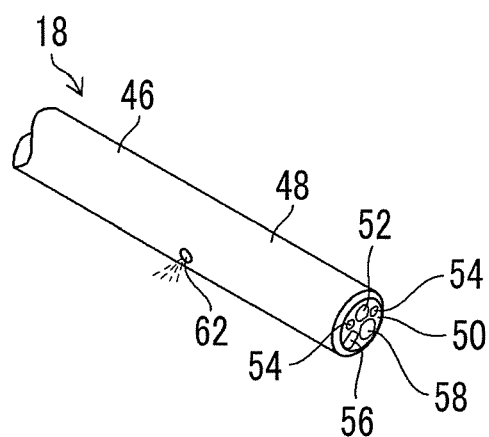
FIG. 2 is an enlarged perspective view illustrating a distal end portion of an insertion part.

FIG. 2 is an enlarged perspective view illustrating the distal end portion 48 of the insertion part 18.

As illustrated in FIG. 2, the distal end surface 50 of the distal end portion 48 is provided with an observation window 52, a pair of illumination windows 54, an air supply and water supply nozzle 56, and a forceps port 58. In the distal end portion 48, an imaging element (not illustrated) is provided behind the observation window 52. An observation image is formed on the imaging element and is photoelectrically converted. A signal cable (not illustrated) is connected to the imaging element, and the signal cable is connected to the processor 30 via the insertion part 18, the hand operation part 16, and the universal cable 20, which are described above. Therefore, an electric signal indicating the observation image photoelectrically converted by the imaging element is output to the processor 30, and then is output to the monitor 60 after the signal is appropriately processed in the processor. Accordingly, the observation image is displayed on the monitor 60.

A light exit end of the light guide (not illustrated) is disposed behind each of the pair of illumination windows 54 in the distal end portion 48. A light incident end of each light guide is connected to the light source device 24. Accordingly, an observed part is irradiated with illumination light supplied from the light source device 24 to the light incident end of each light guide through the pair of illumination windows 54.

An air supply suction port 62 is provided in an outer circumferential surface of the distal end portion 48. The air supply suction port 62 communicates with the balloon air supply port 42 described above via the air supply tube (not illustrated) inserted from the inside of the insertion part 18 to the connector 21A. Therefore, air is blown out from the air supply suction port 62 of the distal end portion 48 by supplying air to the balloon air supply port 42. In addition, air is sucked from the air supply suction port 62 of the distal end portion 48 by sucking air from the balloon air supply port 42.

Figure 3:
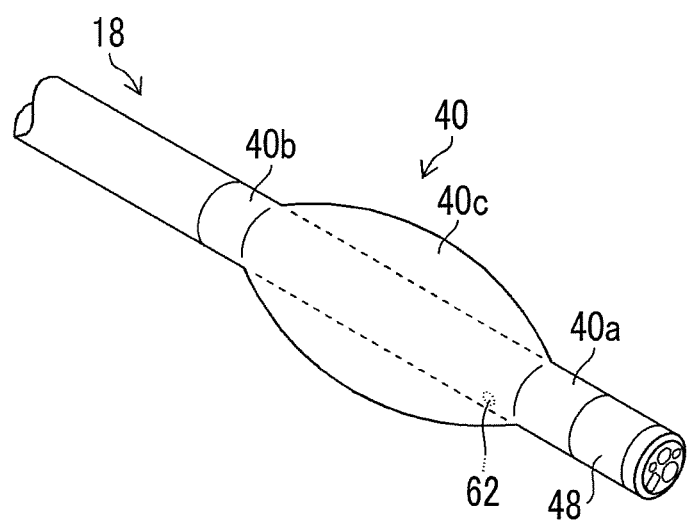
FIG. 3 is an enlarged perspective view of the insertion part on which a balloon is mounted.

FIG. 3 is an enlarged perspective view of the insertion part 18 on which the balloon 40 is mounted.

As illustrated in FIG. 3, the balloon 40 formed of various types of elastic bodies is attachably and detachably mounted on the distal end portion 48 of the insertion part 18. The balloon 40 has a bulging part 40c at a center thereof and mounting parts 40a and 40b on an insertion part distal end side and an insertion part proximal end side thereof. In a state where the air supply suction port 62 is disposed on an inner side of the bulging part 40c of the balloon 40, each of the mounting parts 40a and 40b is fixed to the distal end portion 48 through a known method.

The bulging part 40c of the balloon 40 mounted as described above is inflated into a substantially spherical shape by blowing air from the air supply suction port 62, and the bulging part 40c is deflated by sucking air from the air supply suction port 62.

Figure 4:
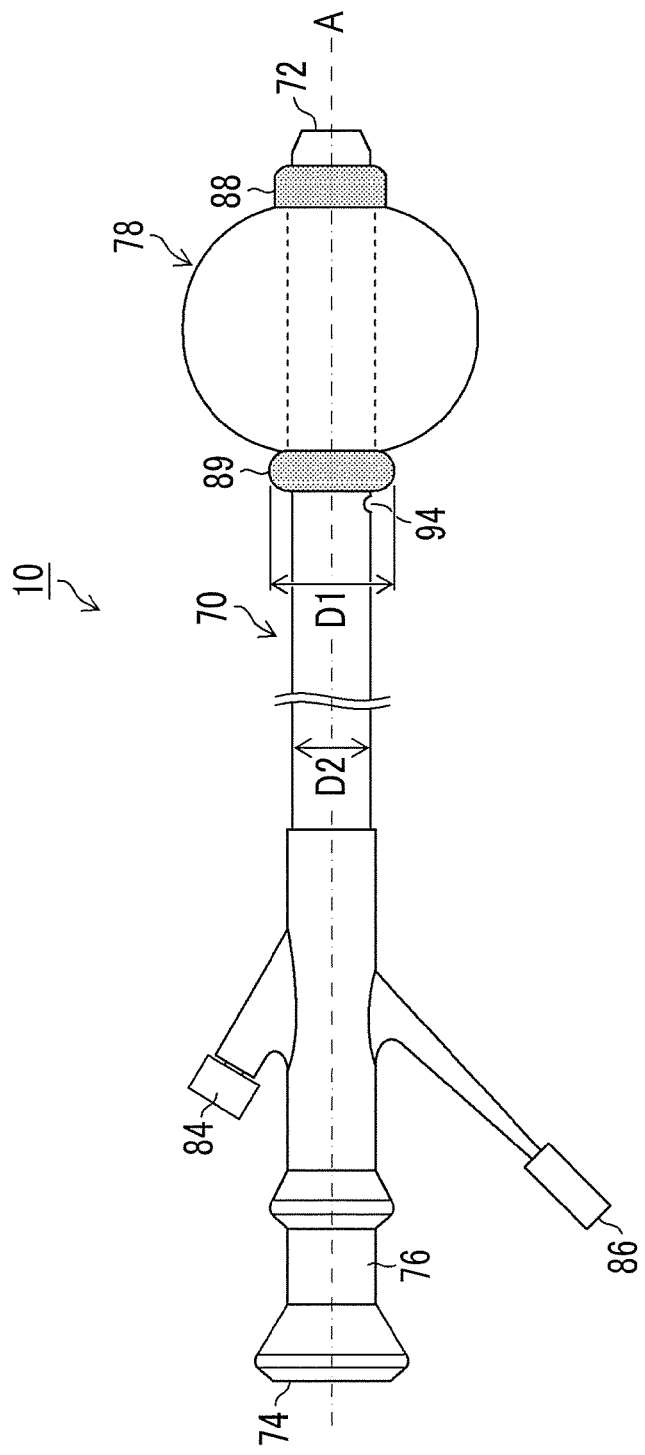
FIG. 4 is a side view of the overtube.

FIG. 4 is a side view of the overtube 10. In addition, FIG. 5 is a cross sectional view of the overtube 10 in a state where the insertion part 18 is inserted.

Figure 5:
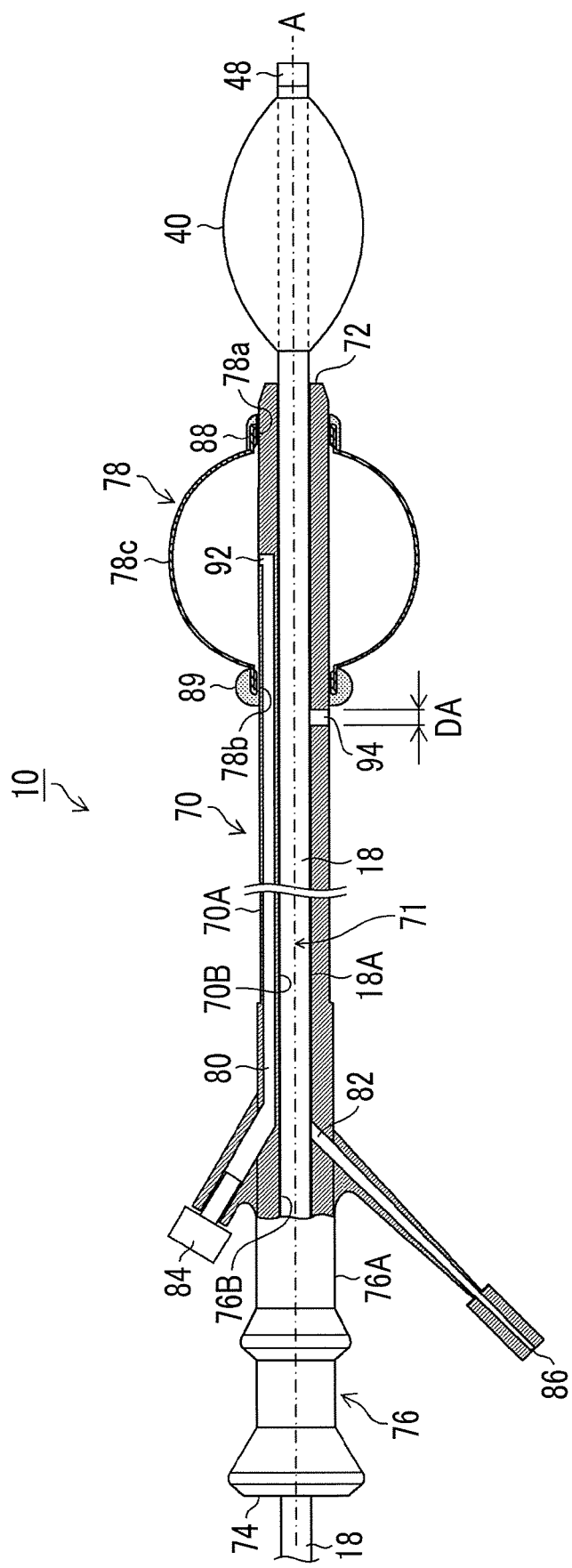
FIG. 5 is a cross sectional view of the overtube in a state where the insertion part is inserted.

As illustrated in FIGS. 4 and 5, the overtube 10 has an overtube body 70. The overtube body 70 is formed of various flexible materials in a tubular shape, has a distal end 72, a proximal end 74, and a central axis A, and the insertion part 18 of the endoscope 14 is inserted thereto. The overtube body 70 has an inner diameter slightly larger than an outer diameter of the insertion part 18. Hereinafter, in the description of each part of the overtube 10, the "distal end side" of each part indicates a side of a direction of the distal end 72, and the "proximal end side" of each part indicates a side of a direction of the proximal end 74.

On a proximal end side of the overtube body 70, there is a gripping part 76 to be gripped by an operator. The gripping part 76 is formed of various types of hard materials in a tubular shape. For this reason, an outer circumferential surface 70A of the overtube body 70 includes a gripping part outer circumferential surface 76A of the gripping part 76, and an inner circumferential surface 70B of the overtube body 70 includes a gripping part inner circumferential surface 76B of the gripping part 76. The insertion part 18 of the endoscope 14 is inserted into the overtube body 70 from a gripping part 76 side. On the other hand, the balloon 78 forming of various types of elastic bodies is mounted on the outer circumferential surface 70A on the distal end side of the overtube body 70.

An insertion passage 71 into which the insertion part 18 of the endoscope 14 is inserted is formed by the inner circumferential surface 70B of the overtube body 70. In addition, an air supply and discharge pipe line 80 and a liquid pipe line 82 are formed between the outer circumferential surface 70A and the inner circumferential surface 70B of the overtube body 70.

The air supply and discharge pipe line 80 is formed along the central axis A and is opened as an air supply suction port 92 on the outer circumferential surface 70A positioned on an inner side of the balloon 78. In addition, the liquid pipe line 82 is formed to penetrate from the gripping part outer circumferential surface 76A to the gripping part inner circumferential surface 76B. The liquid pipe line 82 is a pipe line for supplying a lubricant such as water between the inner circumferential surface 70B including the gripping part inner circumferential surface 76B and an outer circumferential surface 18A of the insertion part 18.

A balloon air supply port (overtube) 84 connected to the air supply and discharge pipe line 80 and a liquid supply port 86 connected to the liquid pipe line 82 are provided in the gripping part outer circumferential surface 76A.

The balloon air supply port (overtube) 84 is connected to the balloon control device 100 to be described later via a tube 106 to be described later (refer to FIG. 1). On the other hand, although not illustrated, a lubricant supply unit such as a syringe is connected to the liquid supply port 86. The liquid supply port 86 hangs downward in a gravity direction in a state of being connected to the lubricant supply unit. For this reason, the liquid supply port 86 is positioned below the balloon air supply port (overtube) 84 in the gravity direction in a state where the gripping part 76 is gripped by an operator.

The balloon 78 is mounted on the outer circumferential surface 70A in a state of being penetrated by the overtube body 70, and is configured by a bulging part 78c at a center thereof and mounting parts 78a and 78b on the distal end side and the proximal end side thereof.

A part of the mounting part 78a on the distal end side is folded back to the outer circumferential surface 70A toward the proximal end side. The mounting part 78a is fixed to the outer circumferential surface 70A of the overtube body 70 by a bonding fixing part 88 made of an adhesive. The bonding fixing part 88 is formed in an annular shape following a circumferential direction of the outer circumferential surface 70A to cover the mounting part 78a and the outer circumferential surface 70A around the mounting part 70A.

A part of the mounting part 78b on the proximal end side (corresponds to an end part of the balloon according to the embodiment of the present invention) is folded back to the outer circumferential surface 70A toward the distal end side. The mounting part 78b is fixed to the outer circumferential surface 70A of the overtube body 70 by an annular bonding fixing part 89 (corresponds to a fixing part and a protruding part according to the embodiment of the present invention) made of an adhesive. The bonding fixing part 89 is formed in an annular shape following the circumferential direction of the outer circumferential surface 70A to cover the mounting part 78b and the outer circumferential surface 70A around the mounting part. In addition, as will be described later in detail, a cross section of the bonding fixing part 89 along the central axis A is formed in a protruding shape (arch shape). Further, an outer diameter D1 of the bonding fixing part 89 is formed to be larger than an outer diameter D2 of the outer circumferential surface 70A.

The air supply suction port 92 described above is opened on the outer circumferential surface 70A positioned inside the bulging part 78c. Therefore, in a case where air is supplied from the balloon air supply port (overtube) 84, the air is blown out from the air supply suction port 92 via the air supply and discharge pipe line 80, and the bulging part 78c is inflated. In addition, in a case where air is sucked from the balloon air supply port (overtube) 84, the air is blown out from the air supply suction port 92 via the air supply and discharge pipe line 80, and the bulging part 78c is deflated.

Figure 6:
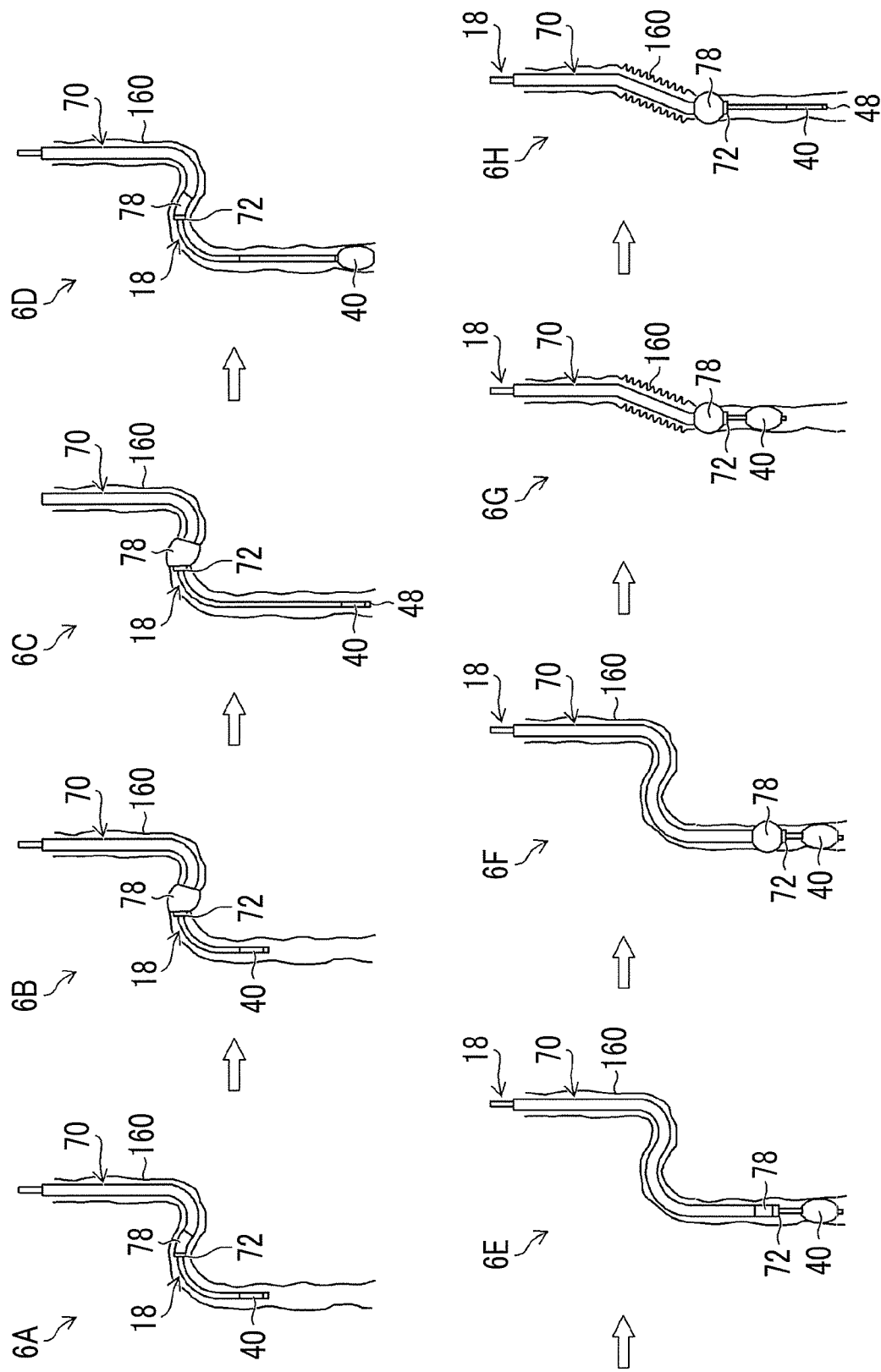
FIG. 6 is an explanatory view illustrating an example of an insertion method of inserting the insertion part of an endoscope into a lumen of a digestive tract.

In the outer circumferential surface 70A of the overtube body 70, a ventilation hole 94 is opened at a position on the proximal end side of the balloon 78 and at a position inserted into the lumen 160 (refer to FIG. 6). The ventilation hole 94 allows the outer circumferential surface 70A and the inner circumferential surface 70B to communicate (penetrate) with each other. The insertion passage 71 of the insertion part 18, which is formed by the inner circumferential surface 70B, communicates with the outside of the body on the proximal end side of the overtube body 70. For this reason, the ventilation hole 94 communicates with the outside of the body via the insertion passage 71 of the insertion part 18.

It is preferable that the ventilation hole 94 has a circular shape and a diameter DA (refer to FIG. 9) of 1 mm to 5 mm. By making the diameter DA of the ventilation hole 94 1 mm or more, the ventilation hole 94 is prevented from being clogged by a residue in the lumen 160.

On the other hand, by making the diameter DA of the ventilation hole 94 5 mm or less, a decrease in the strength of the overtube body 70 can be prevented. As a result, a kink (buckling) of the overtube body 70 is prevented. In addition, the infiltration of a residue from the ventilation hole 94 into the overtube body 70 can be suppressed. Accordingly, a decrease in relative slipperiness between the overtube 10 and the insertion part 18 attributable to the infiltration of the residue is prevented.

Further, by making the ventilation hole 94 circular, a decrease in the strength and a kink of the overtube body 70 can be prevented compared to a case where the ventilation hole 64 is formed in a long hole shape following a circumferential direction of the overtube body 70. Instead of making the ventilation hole 94 circular, the ventilation hole 64 may be formed in a long hole shape following a direction of the central axis A.

Referring back to FIG. 1, the balloon control device 100 is connected to the balloon air supply port 42 of the endoscope 14 (connector 21A) via a tube 104, is connected to the balloon air supply port (overtube) 84 of the overtube body 70 via the tube 106, and is also connected to a hand switch 102. The balloon control device 100 supplies air to each of the balloons 40 and 78 or sucks air in each of the balloons 40 and 78 according to a control signal from the hand switch 102. Accordingly, the balloons 40 and 78 are individually inflated and deflated.

Next, an insertion method of the insertion part 18 of the endoscope 14 and the overtube body 70 using the balloons 40 and 78 respectively will be described. FIG. 6 is an explanatory view illustrating an example of an insertion method of inserting the insertion part 18 of the endoscope 14 into the lumen 160 of the digestive tract.

First, as shown with a reference sign 6A of FIG. 6, an operator inserts the insertion part 18 into the lumen 160 from the anus or the mouth via the pylorus in a state where the insertion part 18 is covered with the overtube body 70. At this time, the balloon 40 and the balloon 78 are both in a deflated state. Then, the operator inserts the distal end 72 of the overtube body 70 to a bent part of the lumen 160.

Next, as shown with a reference sign 6B of FIG. 6, air is supplied from the balloon control device 100 (refer to FIG. 1) to the balloon 78 to inflate the balloon 78. Accordingly, the balloon 78 is locked into a lumen inner wall surface 160A (refer to FIG. 7), which is an inner wall surface of the lumen 160, and the distal end 72 of the overtube body 70 is fixed to the lumen 160.

Next, as shown with a reference sign 6C of FIG. 6, the operator inserts only the insertion part 18 of the endoscope 14 into a deep portion of the lumen 160. Then, as shown with a reference sign 6D of FIG. 6, air is supplied from the balloon control device 100 to the balloon 40 to inflate the balloon 40. Accordingly, the balloon 40 is fixed to the lumen 160.

Next, after the balloon 78 is deflated by sucking air from the balloon 78 by the balloon control device 100, the operator pushes the overtube body 70 to be inserted along the insertion part 18 as shown with a reference sign 6E in FIG. 6. Then, after the distal end 72 of the overtube body 70 is inserted to the vicinity of the balloon 40, air is supplied from the balloon control device 100 to the balloon 78 to inflate the balloon 78 as shown with a reference sign 6F of FIG. 6. Accordingly, the balloon 78 is locked into the lumen inner wall surface 160A (refer to FIG. 7), and the distal end 72 of the overtube body 70 is fixed to the lumen 160.

Next, as shown with a reference sign 6G in FIG. 6, the operator operates the overtube 10 to be pulled to a hand side. Accordingly, the lumen 160 is dragged to the hand side and comes into a deflated state.

Figure 7:
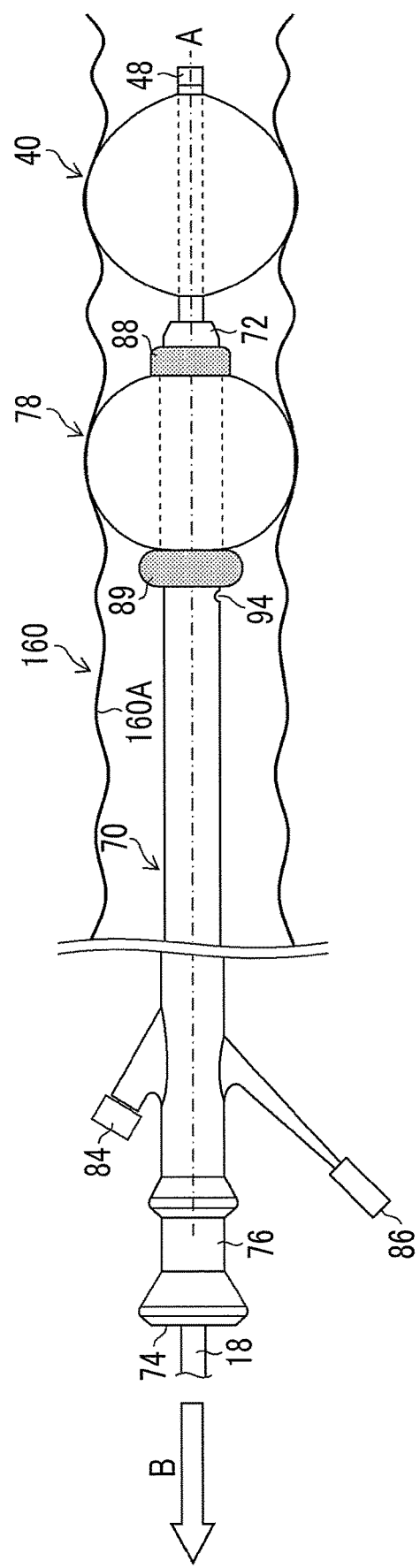
FIG. 7 is an enlarged explanatory view illustrating a state immediately before an operator operates the overtube to be pulled to a hand side.
Figure 8:
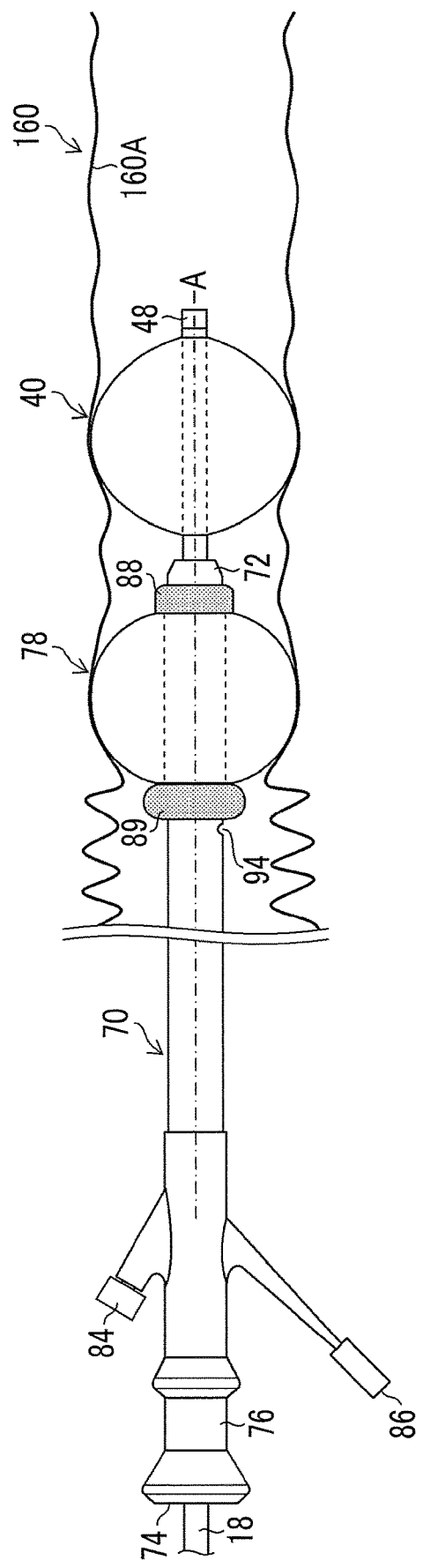
FIG. 8 is an enlarged explanatory view illustrating a state where the operator operates the overtube to be pulled to the hand side.

FIG. 7 is an enlarged explanatory view illustrating a state immediately before the operator operates the overtube 10 to be pulled to the hand side, and is a view corresponding to a reference sign 6F of FIG. 6. In addition, FIG. 8 is an enlarged explanatory view illustrating a state where the operator operates the overtube 10 to be pulled to the hand side, and is a view corresponding to a reference sign 6G of FIG. 6.

In a case where the operator operates the overtube body 70 to be pulled to the hand side (arrow-B direction) from the state illustrated in FIG. 7, a gas accumulated in a region formed by the balloon 78 and the lumen inner wall surface 160A on the proximal end side of the balloon 78 is discharged from the proximal end side thereof to the outside of the body via the ventilation hole 94 and the overtube body 70. Accordingly, as illustrated in FIG. 8, the lumen 160 can be dragged to the hand side without pressing the lumen 160.

Referring back to FIG. 6, as shown with a reference sign 6H, the balloon control device 100 sucks air from the balloon 40 to deflate the balloon 40. Then, the operator again inserts the distal end portion 48 of the insertion part 18 into the deep portion of the lumen 160. That is, the insertion operation shown with the reference sign 6C of FIG. 6 is performed again. Accordingly, the distal end portion 48 of the insertion part 18 can be inserted into the deep portion of the lumen 160. Hereinafter, by repeatedly executing the operations shown with the reference signs 6A to 6H of FIG. 6, the distal end portion 48 of the insertion part 18 can be inserted into a deeper portion of the lumen 160.

Figure 9:
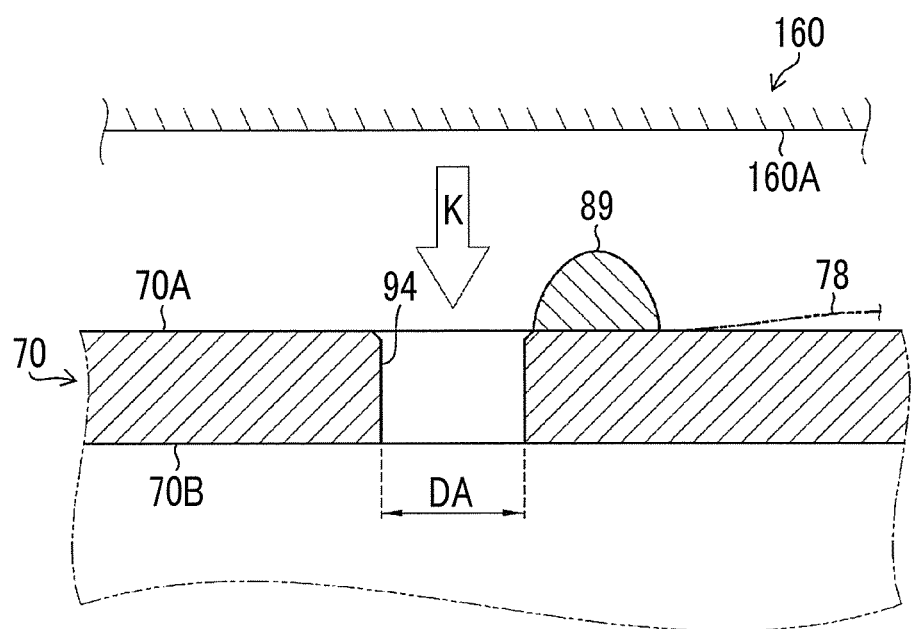
FIG. 9 is a cross sectional view of a bonding fixing part and a ventilation hole taken along a direction of a central axis of an overtube body.
Figure 10:
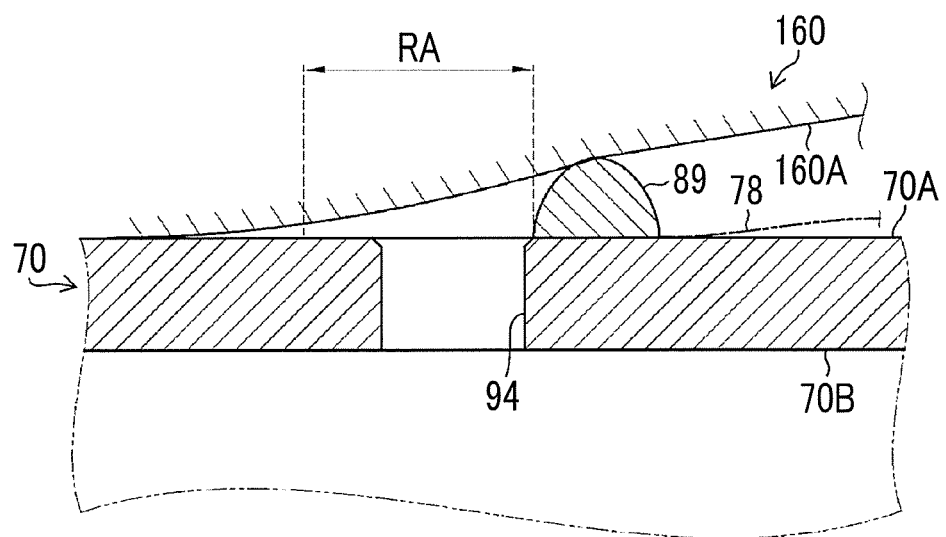
FIG. 10 is an explanatory view for describing a function of the bonding fixing part.
Figure 11:
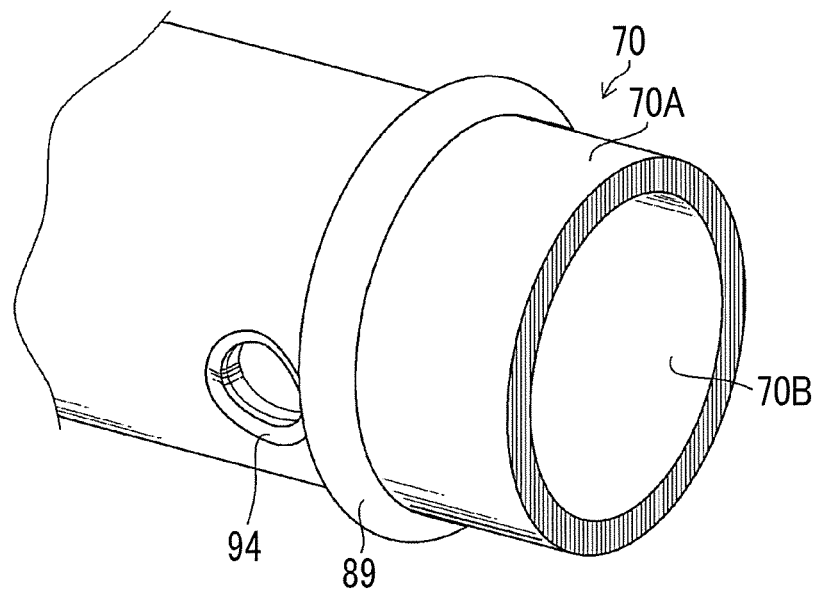
FIG. 11 is a perspective view of the bonding fixing part and the ventilation hole in a state where the balloon is removed from the overtube body.

FIG. 9 is a cross sectional view of the bonding fixing part 89 and the ventilation hole 94 taken along the direction of the central axis A of the overtube body 70. FIG. 10 is an explanatory view for describing a function of the bonding fixing part 89. FIG. 11 is a perspective view of the bonding fixing part 89 and the ventilation hole 94 in a state where the balloon 78 is removed from the overtube body 70.

As illustrated in FIGS. 9 to 11, the bonding fixing part 89 made of an adhesive is aimed in an annular shape (ring shape) in the circumferential direction of the outer circumferential surface 70A, and a cross section thereof taken along the central axis A has a shape protruding in an arch shape toward a radially outer side of the overtube body 70. For this reason, as illustrated in FIG. 4 described above, the outer diameter D1 of the bonding fixing part 89 is formed to be larger than the outer diameter D2 of the outer circumferential surface 70A.

In addition, the cross section of the bonding fixing part 89 is formed in an arch shape. Accordingly, in a state where the overtube body 70 is inserted in the lumen 160, a surface of the bonding fixing part 89 facing the lumen inner wall surface 160A is formed as a curved surface. For this reason, in a case where the bonding fixing part 89 is in contact with the lumen inner wall surface 160A, the bonding fixing part 89 is prevented from exerting any effect on the lumen inner wall surface 160A.

In a case where one of the lumen inner wall surface 160A or the overtube body 70 (a portion where the bonding fixing part 89 is formed) relatively approaches the other as shown with an arrow K of FIG. 9, the bonding fixing part 89 formed on the outer circumferential surface 70A comes into contact with the lumen inner wall surface 160A as illustrated in FIG. 10. Accordingly, a region where a gap is secured between the lumen inner wall surface 160A and the ventilation hole, that is, a contact restricting region where contact with the lumen inner wall surface 160A is restricted by the bonding fixing part 89 (a region that does not come into contact with the lumen inner wall surface 160A) is provided in a peripheral portion of the outer circumferential surface 70A to the bonding fixing part 89.

Therefore, in the embodiment, on the outer circumferential surface 70A, the ventilation hole 94 described above is formed on the proximal end side of the bonding fixing part 89 (the proximal end side of the balloon 78) and on a peripheral portion of the bonding fixing part 89. The "peripheral portion" herein is a region RA where a gap is secured between the lumen inner wall surface 160A and the ventilation hole in the outer circumferential surface 70A by contact between the bonding fixing part 89 and the lumen inner wall surface 160A. The region RA has a shape corresponding to the annular bonding fixing part 89, that is, an annular shape following the circumferential direction of the outer circumferential surface 70A, and is a region having a width from the bonding fixing part 89 toward the proximal end side. A range of the region RA increases or decreases according to a height, a width, and a shape of the bonding fixing part 89, particularly, the height from the outer circumferential surface 70A. The region RA is acquired through an experiment or a simulation.

As described above, in the embodiment, by forming the ventilation hole 94 in the peripheral portion of the bonding fixing part 89, the bonding fixing part 89 functions as a spacer restricting contact between an opening edge portion of the ventilation hole 94 and the lumen inner wall surface 160A. Therefore, the contact of the opening edge portion of the ventilation hole 94 with the lumen inner wall surface 160A is prevented. In addition, since the gap is secured between the ventilation hole 94 and the lumen inner wall surface 160A, the ventilation hole 94 communicates with the inside of the lumen 160 which is on the proximal end side of the balloon 78 via the gap. For this reason, the function of the ventilation hole 94 is not impaired by the bonding fixing part 89. Accordingly, in a case where an operator operates the overtube 10 to be pulled, a gas inside the lumen 160 can be discharged from the ventilation hole 94 to the outside of the body. For this reason, a pressure inside the lumen 160 (an internal pressure of the intestinal tract) can be decreased, and the obstruction of dragging the lumen 160 to the hand side is prevented.

In addition, since the bonding fixing part 89 can perform both of the fixing of the mounting part 78b of the balloon 78 and the prevention of contact of the opening edge portion of the ventilation hole 94 with the lumen inner wall surface 160A, an increase in the number of components of the overtube 10 is suppressed.

Although the bonding fixing part 89 that bonds and fixes the mounting part 40b of the balloon 78 to the outer circumferential surface 70A is used as the protruding part according to the embodiment of the present invention in the first embodiment, an annular protruding part (not illustrated) having the same shape as the bonding fixing part 89 may be formed at a position on the outer circumferential surface 70A, which corresponds to a peripheral portion of the ventilation hole 94, according to an opening position of the ventilation hole 94 on the outer circumferential surface 70A.

The "peripheral portion" of the ventilation hole 94 is a region where the gap is secured between the ventilation hole 94 and the lumen inner wall surface 160A by contact between the annular protruding part and the lumen inner wall surface 160A.

Although the mounting part 78b on the proximal end side of the balloon 78 is fixed on the outer circumferential surface 70A by the bonding fixing part 89 made of an adhesive in the first embodiment, the mounting part may be fixed through various types of known methods such as heat welding or may be fixed by various types of separate annular members. In this case, shapes of various fixing parts that fix the mounting part 78b onto the outer circumferential surface 70A is formed in the substantially same shape as the bonding fixing part 89. The same applies to a second embodiment to be described later.

Second Embodiment

Figure 12:
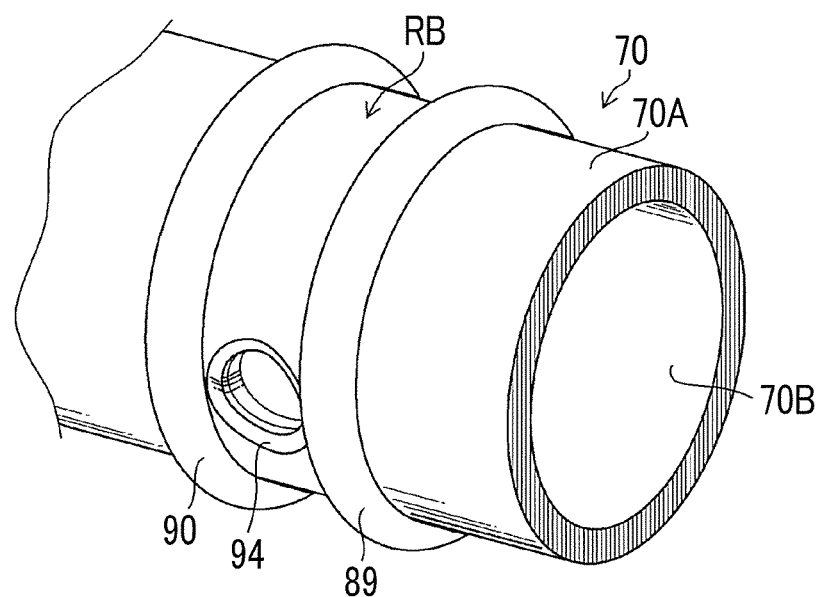
FIG. 12 is a perspective view of a region where a ventilation hole of an overtube according to a second embodiment is formed in a state where a balloon is removed.
Figure 13:
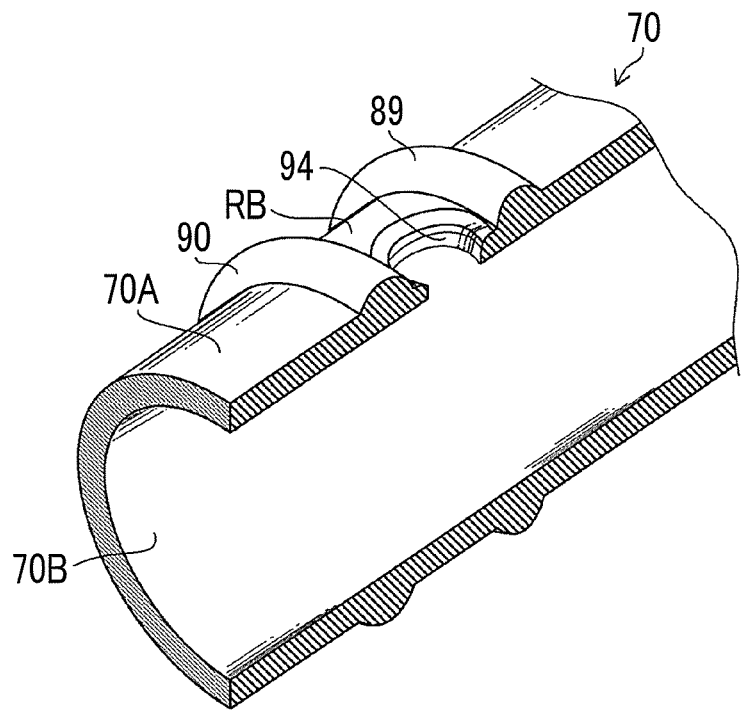
FIG. 13 is a cross sectional view of the region where the ventilation hole illustrated in FIG. 12 is formed.

FIG. 12 is a perspective view of a region where the ventilation hole 94 of the overtube 10 according to the second embodiment is formed in a state where the balloon 78 is removed. FIG. 13 is a cross sectional view of the region where the ventilation hole 94 illustrated in FIG. 12 is formed. The overtube 10 of the second embodiment has basically the same configuration as the overtube 10 of the first embodiment except that an annular protruding part 90 is formed on the outer circumferential surface 70A of the overtube body 70. For this reason, components, which are the same as components in the first embodiment in terms of a function or a configuration, will be assigned with the same reference signs, and description thereof will be omitted.

As illustrated in FIGS. 12 and 13, the annular protruding part 90 functions as the protruding part according to the embodiment of the present invention. The annular protruding part 90 is provided on the outer circumferential surface 70A at a position on the proximal end side of the ventilation hole 94. In addition, the annular protruding part 90 has the substantially same shape as the bonding fixing part 89 described above, is formed in an annular shape following the circumferential direction of the outer circumferential surface 70A of the overtube body 70, and has a cross section along the central axis A, which is formed in an arch shape. That is, on the outer circumferential surface 70A of the second embodiment, the bonding fixing part 89 and the annular protruding part 90 are formed at an interval along the central axis A, and the ventilation hole 94 is opened at a position between the bonding fixing part 89 and the annular protruding part 90.

As the bonding fixing part 89 described above, the annular protruding part 90 comes into contact with the lumen inner wall surface 160A in a case where one of the lumen inner wall surface 160A or the overtube body 70 relatively approaches the other. For this reason, in the second embodiment, both of the bonding fixing part 89 and the annular protruding part 90 come into contact with the lumen inner wall surface 160A, that is, come into contact with the lumen inner wall surface 160A at two points in the direction of the central axis A. Therefore, by adjusting at least one of heights of the bonding fixing part 89 and the annular protruding part 90 or an interval between the bonding fixing part 89 and the annular protruding part 90, a region RB between the bonding fixing part 89 and the annular protruding part 90 in the outer circumferential surface 70A becomes a region where the gap is secured between the lumen inner wall surface 160A and the ventilation hole (the region that does not come into contact with the lumen inner wall surface 160A). The heights of the bonding fixing part and the annular protruding part and the interval between the bonding fixing part and the annular protruding part are acquired through an experiment or a simulation.

The ventilation hole 94 of the second embodiment is opened at a position corresponding to the "peripheral portion" of both of the bonding fixing part 89 and the annular protruding part 90 in the outer circumferential surface 70A, that is, the region RB where the gap is secured between the lumen inner wall surface 160A and the ventilation hole in the outer circumferential surface 70A by contact between both of the bonding fixing part 89 and the annular protruding part 90 and the lumen inner wall surface 160A.

As described above, since both of the bonding fixing part 89 and the annular protruding part 90 function as spacers restricting contact between the opening edge portion of the ventilation hole 94 and the lumen inner wall surface 160A in the second embodiment, the prevention of contact of the opening edge portion of the ventilation hole 94 with the lumen inner wall surface 160A and the securement of a discharging function of the ventilation hole 94 are achieved as in the first embodiment.

In addition, as in the first embodiment, an increase in the number of components of the overtube 10 is suppressed by using the bonding fixing part 89 as the protruding part according to the embodiment of the present invention.

Although the bonding fixing part 89 is used as the protruding part according to the embodiment of the present invention in the second embodiment, two annular protruding parts 90 may be formed on the outer circumferential surface 70A, instead of using the bonding fixing part 89. Specifically, the annular protruding parts 90 are formed in the peripheral portion of the ventilation hole 94 on the outer circumferential surface 70A, that is, at both of a position on the distal end side and a position on the proximal end side of the ventilation hole 94. The "peripheral portion" of the ventilation hole 94 in this case is a region defined particularly by the height of each of the annular protruding parts 90, and is a region where the gap is secured between the ventilation hole 94 and the lumen inner wall surface 160A by contact between each of the annular protruding parts 90 and the lumen inner wall surface 160A.

The plurality of annular protruding parts 90 may be formed along the central axis A on the outer circumferential surface 70A, and the ventilation hole 94 may be formed between the respective annular protruding parts 90.

Third Embodiment

Figure 14:
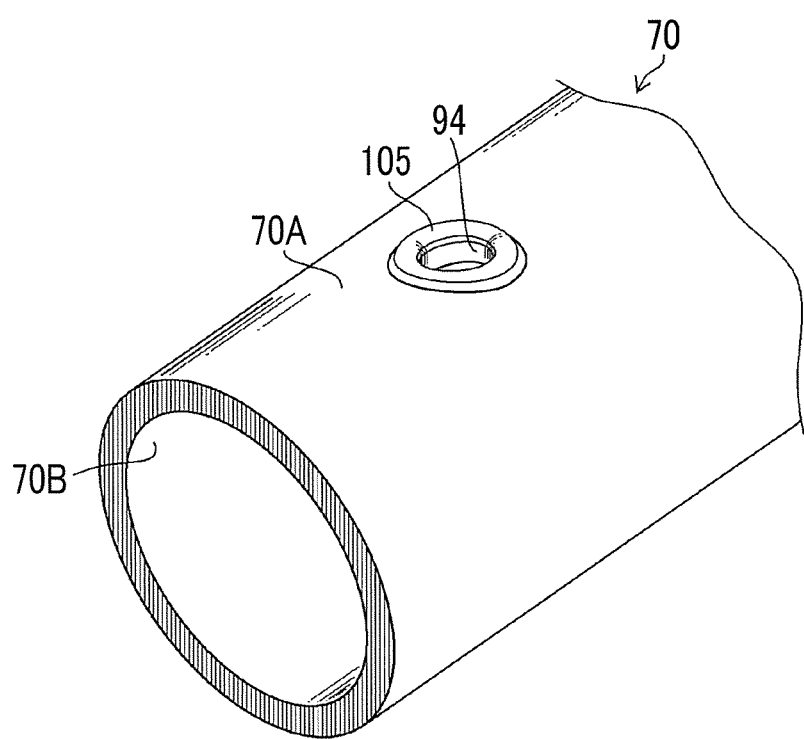
FIG. 14 is a perspective view of a region where a ventilation hole of an overtube of a third embodiment is formed.
Figure 15:
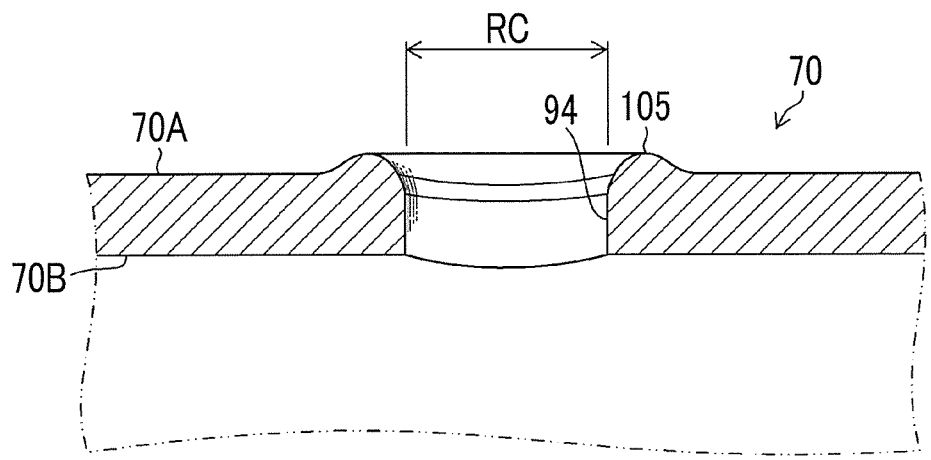
FIG. 15 is a cross sectional view of the ventilation hole of the third embodiment taken along a direction of a central axis of an overtube body.
Figure 16:
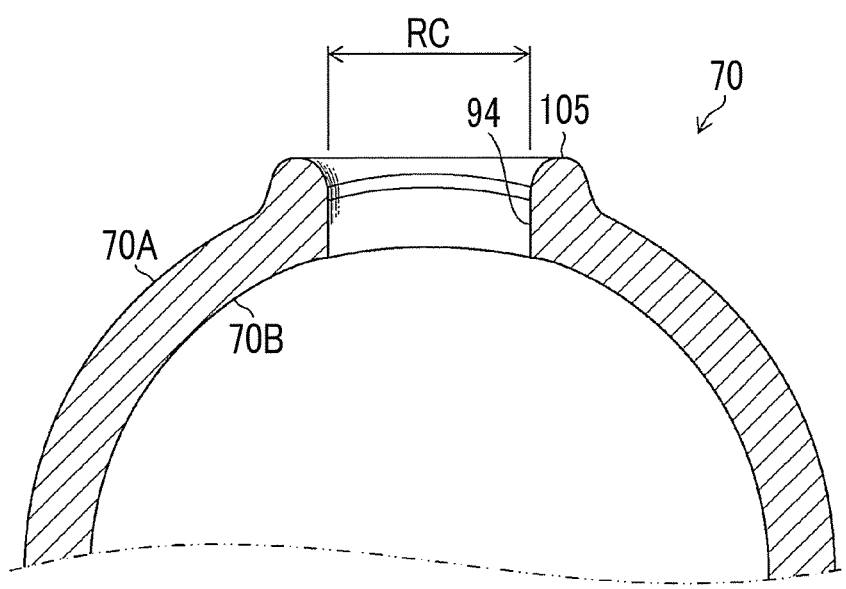
FIG. 16 is a cross sectional view of the ventilation hole of the third embodiment taken along a plane perpendicular to the central axis of the overtube body.

FIG. 14 is a perspective view of a region where the ventilation hole 94 of the overtube 10 of a third embodiment is formed. FIG. 15 is a cross sectional view of the ventilation hole 94 of the third embodiment taken along the direction of the central axis A of the overtube body 70. FIG. 16 is a cross sectional view of the ventilation hole 94 of the third embodiment taken along a plane perpendicular to the central axis A of the overtube body 70.

As illustrated in FIGS. 14 to 16, the overtube 10 of the third embodiment has basically the same configuration as the overtube 10 of the first embodiment except that an annular protruding part 105 (corresponds to the protruding part according to the embodiment of the present invention) different from each of the embodiments is formed on the outer circumferential surface 70A of the overtube body 70. For this reason, components, which are the same as components in the first embodiment in terms of a function or a configuration, will be assigned with the same reference signs, and description thereof will be omitted.

The annular protruding part 105 is formed in an annular shape in the peripheral portion of the ventilation hole 94 along the outer circumferential surface 70A, more specifically, along an opening (opening edge portion) of the ventilation hole 94, and a cross section thereof along a radial direction of the ventilation hole 94 is formed in an arch shape. In a case where one of the lumen inner wall surface 160A or the overtube body 70 relatively approaches the other, the annular protruding part 105 comes into contact with the lumen inner wall surface 160A. For this reason, by adjusting a height of the annular protruding part 105 in particular, a region RC on an inner side of the annular protruding part 105 on the outer circumferential surface 70A becomes a region where the gap is secured between the lumen inner wall surface 160A and the ventilation hole (the region that does not come into contact with the lumen inner wall surface 160A). The height of the annular protruding part 105 is acquired through an experiment or a simulation.

The "peripheral portion" of the ventilation hole 94 in the third embodiment is a region where the gap is secured between the ventilation hole 94 and the lumen inner wall surface 160A on the outer circumferential surface 70A by contact between the annular protruding part 105 and the lumen inner wall surface 160A.

As described above, by forming the annular protruding part 105 in the peripheral portion of the ventilation hole 94 in the third embodiment, the annular protruding part 105 functions as a spacer restricting contact between the opening edge portion of the ventilation hole 94 and the lumen inner wall surface 160A. Therefore, the contact of the opening edge portion of the ventilation hole 94 with the lumen inner wall surface 160A is prevented as in each of the embodiments. In addition, unlike each of the embodiments, since it is not necessary to open the ventilation hole 94 in the vicinity of the bonding fixing part 89, a degree of freedom of the position of the ventilation hole 94 can be increased.

Fourth Embodiment

Figure 17:
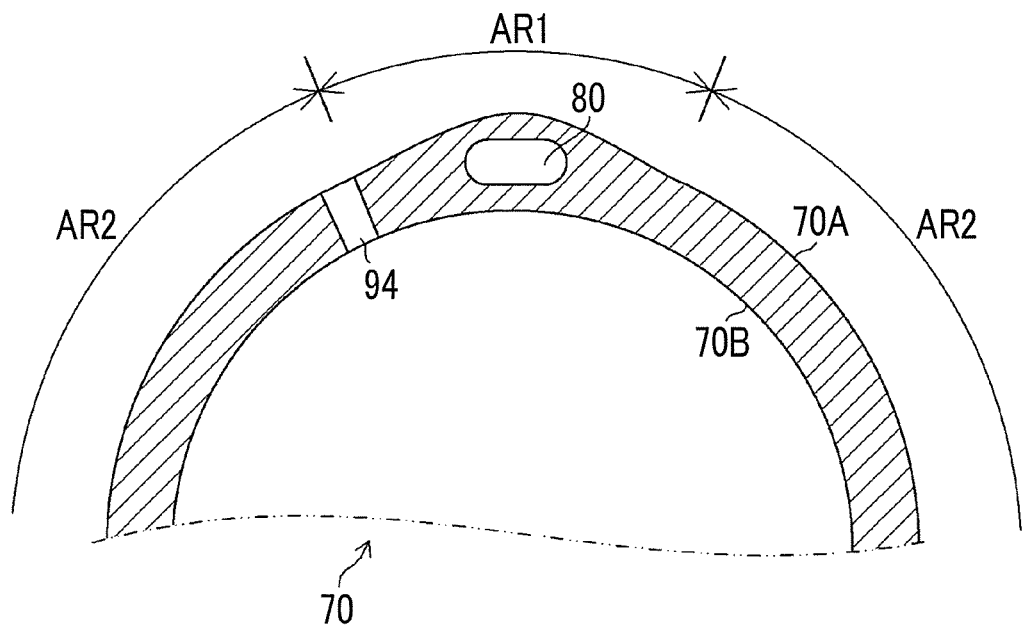
FIG. 17 is a cross sectional view of a ventilation hole of an overtube according to a fourth embodiment taken along a plane perpendicular to a central axis of an overtube body.

FIG. 17 is a cross sectional view of the ventilation hole 94 of the overtube 10 according to a fourth embodiment taken along the plane perpendicular to the central axis A of the overtube body 70. The overtube 10 of the fourth embodiment has basically the same configuration as the overtube 10 of the first embodiment except that a position where the ventilation hole 94 is formed is determined based on the air supply and discharge pipe line 80 in the overtube body 70. For this reason, components, which are the same as components in the first embodiment in terms of a function or a configuration, will be assigned with the same reference signs, and description thereof will be omitted.

As illustrated in FIG. 17, the air supply and discharge pipe line 80 is formed along the central axis A at a position between the outer circumferential surface 70A and the inner circumferential surface 70B of the overtube body 70 (refer to FIG. 5). For this reason, in the outer circumferential surface 70A, a first region AR1 corresponding to a portion where the air supply and discharge pipe line 80 is upheaved higher in an arch shape toward the radially outer side of the overtube body 70 than a second region AR2 corresponding to the other portion. Therefore, in the fourth embodiment, a height (upheaved amount) and a range of the first region AR1 are adjusted by adjusting the position where the air supply and discharge pipe line 80 is formed and the diameter of the air supply and discharge pipe line 80. Accordingly, in a case where the first region AR1 is in contact with the lumen inner wall surface 160A, a gap is secured between the lumen inner wall surface 160A and a peripheral portion of the first region AR1 in the outer circumferential surface 70A. For this reason, the first region AR1 functions as the protruding part according to the embodiment of the present invention.

Thus, in the fourth embodiment, the ventilation hole 94 is opened at the peripheral portion of the first region AR1 on the outer circumferential surface 70A. The peripheral portion of the first region AR1 is a region where a gap is secured between the lumen inner wall surface 160A and the ventilation hole in the outer circumferential surface 70A by contact between the first region AR1 and the lumen inner wall surface 160A.

As described above, by forming the ventilation hole 94 in the peripheral portion of the first region AR1 upheaved by the air supply and discharge pipe line 80 as described above in the fourth embodiment, the first region AR1 functions as a spacer restricting contact between the opening edge portion of the ventilation hole 94 and the lumen inner wall surface 160A. Therefore, the contact of the opening edge portion of the ventilation hole 94 with the lumen inner wall surface 160A is prevented as in each of the embodiments.

Fifth Embodiment

Next, the overtube 10 of a fifth embodiment of the present invention will be described. Although the endoscopy described in each of the embodiments is basically performed by an operator, the endoscopy may be performed with the help of an assistant in some cases. Hereinafter, an example in which the operator and the assistant perform endoscopy will be described.

Figure 18:
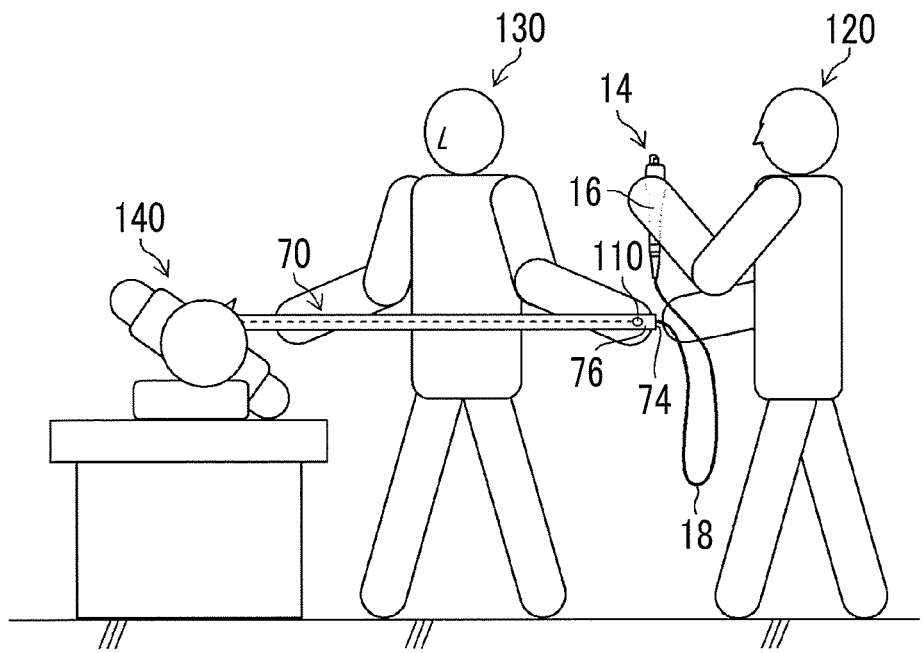
FIG. 18 is an explanatory view schematically illustrating a situation where an operator and an assistant perform endoscopy on a subject.
Figure 19:
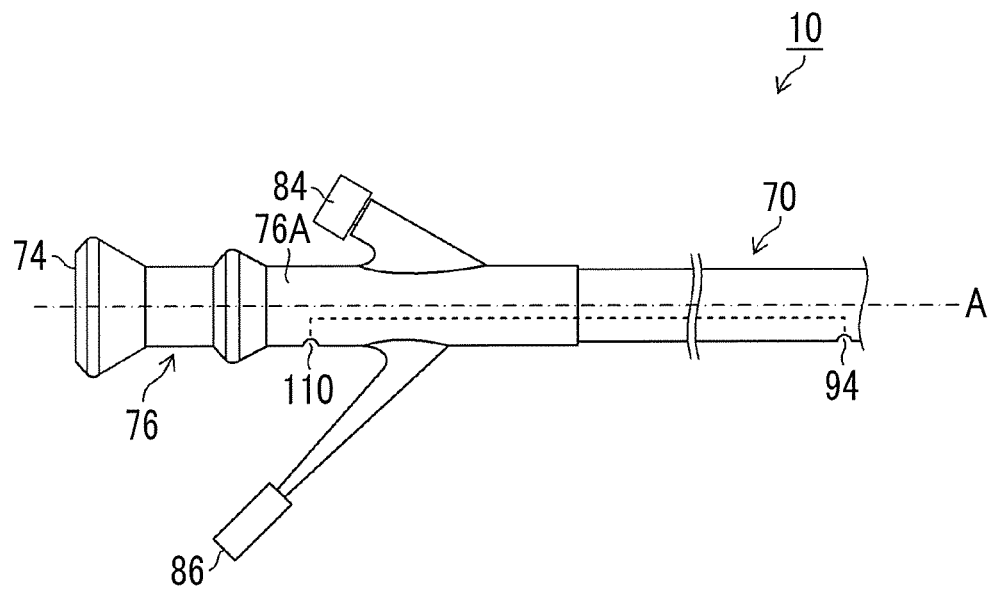
FIG. 19 is a side view of an overtube of a fifth embodiment.

FIG. 18 is an explanatory view schematically illustrating a situation where an operator 120 and an assistant 130 perform endoscopy on a subject 140. In addition, FIG. 19 is a side view of the overtube 10 of the fifth embodiment.

As illustrated in FIG. 18, the operator 120 performs operation of holding the hand operation part 16 of the endoscope 14 with the left hand, holding the insertion part 18 with the right hand, and inserting the insertion part 18 into the lumen 160 of the subject 140 via the overtube body 70. On the other hand, the assistant 130 performs operation of holding the gripping part 76 of the overtube body 70 with the left hand and holding the distal end side of the overtube body 70 with the right hand to insert the overtube body 70 into the lumen 160 of the subject 140.

In such endoscopy, when the assistant 130 operates the overtube body 70 to be pulled, that is, in a case of dragging the lumen 160 to the hand side, a gas and a bodily fluid, which are flowed in the overtube body 70 from the ventilation hole 94 of the overtube body 70, are discharged from the proximal end 74 of the overtube body 70 to the outside in some cases.

In such a case, since the operator 120 faces the proximal end 74 of the overtube body 70, it is desirable that the gas and the bodily fluid (particularly, the bodily fluid) discharged from the proximal end 74 do not adhere to the operator 120.

Thus, in the overtube 10 of the fifth embodiment illustrated in FIG. 19, a gripping part ventilation hole 110 that allows the gripping part outer circumferential surface 76A and the gripping part inner circumferential surface 76B to communicate with each other is opened in the gripping part outer circumferential surface 76A of the gripping part 76. The overtube 10 of the fifth embodiment has basically the same configuration as the overtube 10 of each of the embodiments except that the gripping part ventilation hole 110 is included. Components, which are the same as components in each of the embodiments in terms of a function or a configuration, will be assigned with the same reference signs, and description thereof will be omitted.

The gripping part ventilation hole 110 communicates with both of the ventilation hole 94 and an opening (not illustrated) of the proximal end 74 via the inside of the overtube body 70 (the insertion passage 71 of the insertion part 18). In other words, the ventilation hole 94 communicates with both of the gripping part ventilation hole 110 positioned outside of the body and the opening of the proximal end 74 via the inside of the overtube body 70 (the insertion passage 71).

In the overtube 10 of the fifth embodiment, the gas and the bodily fluid which are flowed in the overtube body 70 from the ventilation hole 94 in a case of dragging the lumen 160 can be discharged to the outside from the gripping part ventilation hole 110 of the gripping part 76. Therefore, by forming the gripping part ventilation hole 110 in the gripping part 76, the operator 120 can perform operation of the endoscope 14 without paying attention to the gas and the bodily fluid discharged from the proximal end 74.

Herein, it is preferable that a position where the gripping part ventilation hole 110 is formed with respect to the gripping part 76 is formed in the vicinity of the balloon air supply port (overtube) 84 to be positioned on the lower side in the gravity direction when the overtube 10 is used. Accordingly, the gas and the bodily fluid, which are discharged from the gripping part ventilation hole 110, are discharged downward as it is. In addition, it is preferable that the gripping part ventilation hole 110 is formed at a position closer to the proximal end side of the overtube body 70 than the liquid pipe line 82 is. Accordingly, the leakage of a lubricant, which is supplied from the liquid supply port 86 into the overtube body 70 via the liquid pipe line 82, from the gripping part ventilation hole 110 can be suppressed.

[Others]

Figure 20:
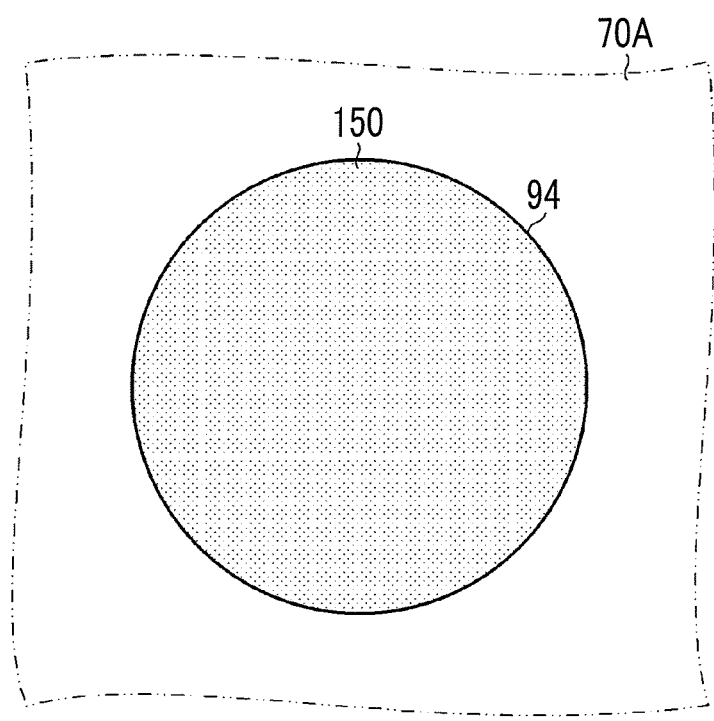
FIG. 20 is a front view of a ventilation hole of another embodiment.

FIG. 20 is a front view of the ventilation hole 94 according to another embodiment. As illustrated in FIG. 20, a porous film 150 may be provided in the ventilation hole 94 in the overtube 10 of each of the embodiments. The porous film 150 is a film that selectively allows a gas to pass therethrough and selectively blocks a bodily fluid and a residue. By providing the porous film 150 in the ventilation hole 94 in this manner, the infiltration of the residue from the ventilation hole 94 into the overtube body 70 can be prevented. Accordingly, a decrease in relative slipperiness between the overtube 10 and the insertion part 18 attributable to the infiltration of the residue can be prevented.

The porous film 150 may be provided in the gripping part ventilation hole 110 illustrated in FIG. 19 of the fifth embodiment described above. Accordingly, only a gas can be discharged from the gripping part ventilation hole 110. As a result, a bodily fluid is prevented from adhering to the operator 120 and the assistant 130.

Although a gas is discharged to the outside of the body from the ventilation hole 94 via the inside of the overtube body 70 (the insertion passage 71 of the insertion part 18 formed by the inner circumferential surface 70B) in each of the embodiments, an air passage 170, through which the gas is discharged without going through the insertion passage 71, may be formed between the outer circumferential surface 70A and the inner circumferential surface 70B.

Figure 21:
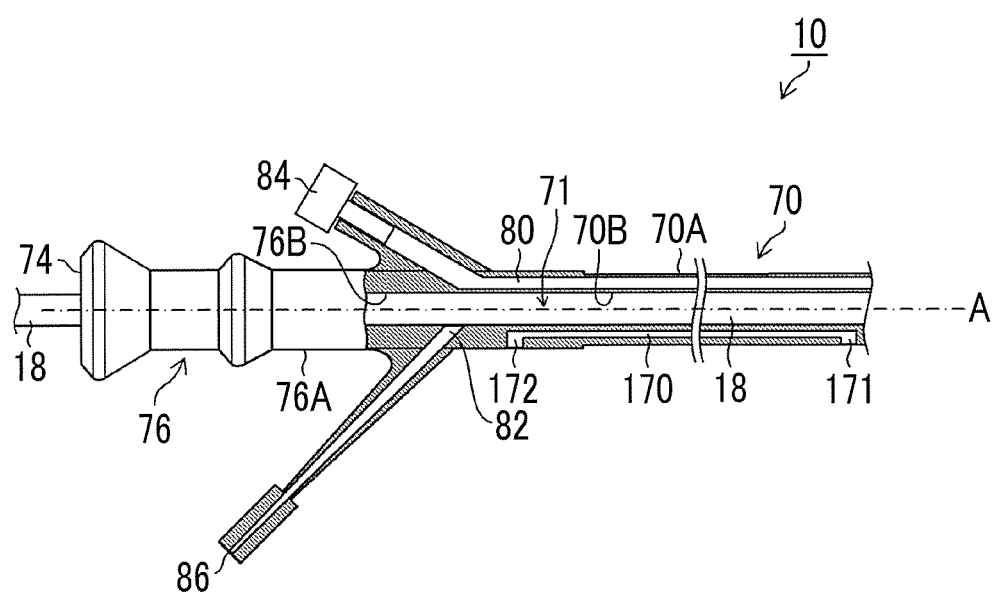
FIG. 21 is a cross sectional view of an air passage.

FIG. 21 is a cross sectional view of the air passage 170. As illustrated in FIG. 21, the air passage 170 is formed along the central axis A between the outer circumferential surface 70A and the inner circumferential surface 70B of the overtube body 70. The distal end side of the air passage 170 is opened as a ventilation hole 171 at a position corresponding to the ventilation hole 94 of each of the embodiments on the outer circumferential surface 70A of the overtube body 70. In addition, the proximal end side of the air passage 170 is opened as a discharge hole 172 in the gripping part outer circumferential surface 76A on the proximal end side of the overtube body 70 (outside of the body). Therefore, the overtube body 70 of FIG. 21 allows a gas in the lumen 160 to be discharged from the discharge hole 172 via the ventilation hole 171 and the air passage 170.

Although one ventilation hole 94 is opened on the outer circumferential surface 70A in each of the embodiments, a plurality of ventilation holes 94 may be opened in the peripheral portion on the outer circumferential surface 70A described in each of the embodiments.

Although the protruding part (the bonding fixing part 89 and the annular protruding parts 90 and 105) of the first embodiment to the third embodiment of the present invention is formed in an annular shape, the protruding part may be formed in various types of shapes such as a single point shape, a multipoint shape, a line shape, a dot array shape, and a mesh shape insofar as the function of the spacer described above can be performed. In addition, in this case, the disposition and number of ventilation holes 94 are adjusted according to the shape of the protruding part.

Although the overtube 10 used in the double-balloon endoscope device 1 has been described as an example in each of the embodiments, the present invention can also be applied to the overtube 10 used in a single-balloon device.

EXPLANATION OF REFERENCES

1: endoscope device
10: overtube
14: endoscope
16: hand operation part
18: insertion part
18A: outer circumferential surface
20: universal cable
21A: connector
21B: connector
24: light source device
30: processor
32: air supply and water supply button
34: suction button
36: shutter button
38: angle knob
39: forceps insertion unit
40: balloon
40a: mounting part
40b: mounting part
40c: bulging part
42: balloon air supply port
44: flexible portion
46: curved portion
48: distal end portion
50: distal end surface
52: observation window
54: illumination window
56: air supply and water supply nozzle
58: forceps port
60: monitor
62: air supply suction port
70: overtube body
70A: outer circumferential surface 70B: inner circumferential surface
71: insertion passage
72: distal end
74: proximal end
76: gripping part
76A: gripping part outer circumferential surface
76B: gripping part inner circumferential surface
78: balloon
78a: mounting part
78b: mounting part
78c: bulging part
80: air supply and discharge pipe line
82: liquid pipe line
84: balloon air supply port (overtube)
86: liquid supply port
88: bonding fixing part
89: bonding fixing part
90: annular protruding part
92: air supply suction port
94: ventilation hole
100: balloon control device
102: hand switch
104: tube
105: annular protruding part
106: tube
110: gripping part ventilation hole
120: operator
130: assistant
140: subject
150: porous film
160: lumen
160A: lumen inner wall surface
170: air passage
171: ventilation hole
172: discharge hole
A: central axis
AR1: first region
AR2: second region
RA: region
RB: region
RC: region

What is claimed is:

1. An overtube comprising:
an overtube body that has a distal end and a proximal end and allows an insertion part of an endoscope, which is to be inserted into a lumen, to be inserted therein;
a balloon that is mounted on an outer circumferential surface of the overtube body;
a protruding part that is formed on the outer circumferential surface; and
an ventilation hole that is formed in the outer circumferential surface and allows the outer circumferential surface and an inner circumferential surface of the overtube body to communicate with each other,
wherein on the outer circumferential surface, the protruding part is peripheral to the ventilation hole,
an air supply and discharge pipe line that allows air to be supplied and discharged into and from an inside of the balloon is formed between the outer circumferential surface and the inner circumferential surface of the overtube body along a central axis of the overtube body,
on the outer circumferential surface, a first region corresponding to a portion where the air supply and discharge pipe line is formed is upheaved higher than a second region corresponding to the other portion, and
the first region of the outer circumferential surface, which is upheaved, is the protruding portion.

2. The overtube according to claim 1,
wherein the ventilation hole is formed closer to a proximal end side of the overtube body than the balloon is.

3. The overtube according to claim 1,
wherein a surface of the protruding part, which faces an inner wall surface of the lumen, is formed by a curved surface.

4. The overtube according to claim 1,
wherein the ventilation hole has a circular shape having a diameter of 1 mm to 5 mm.

5. The overtube according to claim 1,
wherein a porous film that selectively allows air to pass therethrough is provided in the ventilation hole.

6. An overtube comprising:
an overtube body that has a distal end and a proximal end and allows an insertion part of an endoscope, which is to be inserted into a lumen, to be inserted therein;
a balloon that is mounted on an outer circumferential surface of the overtube body;
a protruding part that is formed on the outer circumferential surface; and
an ventilation hole that is formed in the outer circumferential surface and allows the outer circumferential surface and an inner circumferential surface of the overtube body to communicate with each other,
wherein on the outer circumferential surface, the protruding part is peripheral to the ventilation hole,
there is a gripping part on a proximal end side of the overtube body configured to be gripped by an operator,
a gripping part outer circumferential surface of the gripping part is included in the outer circumferential surface, and a gripping part inner circumferential surface of the gripping part is included in the inner circumferential surface, and
the overtube further comprises a gripping part ventilation hole that allows the gripping part inner circumferential surface and the gripping part outer circumferential surface of the gripping part to communicate with each other.

7. The overtube according to claim 6,
wherein an annular fixing part that fixes an end part of the balloon, which is positioned closer to a proximal end side of the overtube body than a bulging part of the balloon is, to the outer circumferential surface is provided on the outer circumferential surface,
an outer diameter of the annular fixing part is formed to be larger than an outer diameter of the outer circumferential surface, and
the protruding part is the annular fixing part.

8. The overtube according to claim 6,
wherein the protruding part has an annular shape that surrounds an opening of the ventilation hole in the outer circumferential surface.

9. The overtube according to claim 6,
wherein a porous film that selectively allows air to pass therethrough is provided in the ventilation hole.

* * * * *